(12) United States Patent
Podhajsky et al.

(10) Patent No.: US 7,443,175 B2
(45) Date of Patent: Oct. 28, 2008

(54) SURGICAL TESTING INSTRUMENT AND SYSTEM

(75) Inventors: Ronald J. Podhajsky, Boulder, CO (US); James H. Orszulak, Nederland, CO (US); Behzad Ghorbani-Elizeh, Boulder, CO (US); David Dumbauld, Atlanta, GA (US)

(73) Assignee: Covidien AG, Neuhausen am Rheinfall (CH)

( * ) Notice: Subject to any disclaimer, the term of this patent is extended or adjusted under 35 U.S.C. 154(b) by 237 days.

(21) Appl. No.: 11/487,295

(22) Filed: Jul. 14, 2006

(65) Prior Publication Data

US 2008/0030206 A1    Feb. 7, 2008

(51) Int. Cl.
*G01R 27/26* (2006.01)
*G01R 27/08* (2006.01)
*A61B 18/04* (2006.01)

(52) U.S. Cl. .................. 324/663; 324/692; 606/34
(58) Field of Classification Search .......... 324/663, 324/658, 649, 600, 692, 691, 76.11, 71.1; 600/442, 506, 547; 606/34, 38; 607/154
See application file for complete search history.

(56) References Cited

U.S. PATENT DOCUMENTS

| | | | |
|---|---|---|---|
| 3,601,126 A | 8/1971 | Estes | |
| 4,126,137 A | 11/1978 | Archibald | |
| 4,281,373 A | 7/1981 | Mabille | |
| 4,416,277 A | 11/1983 | Newton et al. | |
| 4,448,284 A | 5/1984 | Ciabo | |
| 4,494,541 A | 1/1985 | Archibald | |
| 4,651,280 A | 3/1987 | Chang et al. | |
| 4,716,360 A | 12/1987 | Pakulis | |
| 4,749,895 A | 6/1988 | Ruelle | |
| 4,868,769 A * | 9/1989 | Persson | 702/30 |
| 4,899,102 A * | 2/1990 | Hendrick et al. | 324/663 |
| 5,309,110 A * | 5/1994 | O'Neill et al. | 324/674 |
| 6,293,941 B1 | 9/2001 | Strul et al. | |
| 6,511,917 B2 * | 1/2003 | Haji et al. | 438/706 |
| 6,583,631 B2 * | 6/2003 | Park et al. | 324/663 |
| 2002/0038095 A1 | 3/2002 | Tucker | |
| 2003/0183764 A1 | 10/2003 | Bigarre et al. | |
| 2005/0075579 A1 | 4/2005 | Semlyen et al. | |
| 2006/0156984 A1 * | 7/2006 | Nozawa et al. | 118/723 R |

OTHER PUBLICATIONS

Velez et al., "Use of Parallel Plates Measurement Method for Designing and Construction of a Measurement System of Measuring Permittivity in Phantoms in 40Hz to 110MHz Frequencies Range", 2004 1st International Conference on Electrical and Electronics Engineering, pp. 499-504.

* cited by examiner

Primary Examiner—Vincent Q. Nguyen
Assistant Examiner—Hoai-An D Nguyen (57) ABSTRACT

The present disclosure describes an instrument for measuring the dielectric properties of biological tissue. The instrument includes a top electrode assembly and a bottom electrode assembly, the top electrode assembly including a top electrode and at least one shaft adjustably positionable to move the top electrode relative to the bottom electrode assembly, the bottom electrode assembly including a bottom test plate and a bottom electrode. The instrument also includes a testing cylinder coupled to the shaft and having an inner cavity defined therein that houses the top electrode and which is designed to enclose the bottom electrode therein. The testing cylinder is configured to reduce at least one of electric current, magnetic current, stray radiative RF fields and external capacitive leakage currents during activation of the top and bottom electrodes.

25 Claims, 10 Drawing Sheets

SURGICAL TESTING INSTRUMENT AND SYSTEM

TECHNICAL FIELD

The present disclosure relates to a surgical testing instrument. More particularly, the present disclosure relates to an apparatus and system for measuring dielectric properties of biological tissue.

BACKGROUND

Radio frequency or RF energy is commonly used in a variety of different surgical operations. However, body tissues that are subjected to very high levels of RF energy may suffer some residual heat damage. Therefore, prior to the use of RF energy on a particular patient it is often desirable to develop computer simulated heat transfer and electric field models of the heat transfer to tissue using computer programs.

When an electric charge is applied across a material, in this case tissue, a charge and current are created in the material. The density of charge is referred to as the permittivity ($\in$) while the density of current is called the conductivity ($\sigma$). These two properties are largely responsible for the response of different tissue types to an arbitrary RF electric field and should be included in any accurate computer modeling. Moreover, by comparing the electrical properties of healthy and abnormal tissue it may be possible to detect the onset of certain kinds of pathologies or sicknesses.

Testing methodologies exist for determining the permittivity and conductivity of a given material. However, a number of these methodologies contain numerous sources of error that affect the accuracy of the measurement, which may be detrimental to accurate tissue heat transfer modeling.

SUMMARY

The present disclosure relates to an instrument for measuring the dielectric properties of biological tissue and other materials. The instrument includes a top electrode assembly and a bottom electrode assembly, the top electrode assembly including a top electrode and at least one shaft adjustably positionable to move the top electrode relative to the bottom electrode assembly, the bottom electrode assembly including a testing plate and a bottom electrode. The instrument also includes a testing cylinder coupled to the shaft and having an inner cavity defined therein that houses the top electrode and which is designed to enclose the bottom electrode therein. The testing cylinder is configured to reduce at least one of electric current, magnetic current, stray radiative RF fields and external capacitive leakage currents during activation of the top and bottom electrodes.

According to one embodiment of the present disclosure a system for measuring the dielectric properties of biological tissue is provided. The system includes an analyzer configured to measure the properties of the tissue. The system also includes a top electrode assembly and a bottom electrode assembly, the top electrode assembly having a top electrode and at least one shaft adjustably positionable to move the top electrode relative to the bottom electrode assembly, the bottom electrode assembly having a testing plate and a bottom electrode. In accordance with this embodiment a testing cylinder is coupled to the shaft and includes an inner cavity defined therein that houses the top electrode and which is designed to enclose the bottom electrode therein, the testing cylinder is configured to reduce at least one of electric current, magnetic current, stray radiative RF fields and external capacitive leakage currents during activation of the top and bottom electrodes. The system further includes a graphical user interface configured to control the analyzer.

The present disclosure also relates to a method for measuring the dielectric properties of biological tissue is provided. The method includes the step of providing a top electrode assembly and a bottom electrode assembly, the top electrode assembly including a top electrode and at least one shaft adjustably positionable to move the top electrode relative to the bottom electrode assembly, the bottom electrode assembly including a bottom test plate and a bottom electrode. The method also includes the step of coupling a testing cylinder to the shaft, the testing cylinder having an inner cavity defined therein that houses the top electrode and which is designed to enclose the bottom electrode therein, the testing cylinder being configured to reduce at least one of electric current, magnetic current, stray radiative RF fields and external capacitive leakage currents during activation of the top and bottom electrodes. The method further includes the step of connecting an analyzer to the top electrode assembly and the bottom electrode assembly, the analyzer being configured to measure and analyze the dielectric properties of biological tissue.

According to a further aspect of the present disclosure a method for measuring the dielectric properties of biological tissue is disclosed. The method includes the steps of providing a top electrode assembly, a bottom electrode assembly and a testing plate. The top electrode assembly includes a top electrode and at least one shaft adjustably positionable to move the top electrode relative to the bottom electrode assembly. The bottom electrode assembly includes a bottom electrode. The testing plate is disposed between the top electrode assembly and a bottom electrode assembly and includes a selectively conformable insert cavity therein. The method also includes the step of inserting a tissue sample into the selectively conformable insert cavity and forming the tissue sample by cutting any excess tissue to fit the tissue sample into the insert cavity. The method further includes the step of coupling a testing cylinder to the shaft. The testing cylinder includes an inner cavity defined therein that houses the top electrode and is designed to enclose the bottom electrode therein. The testing cylinder is configured to reduce at least one of electric current, magnetic current, stray radiative RF fields and external capacitive leakage currents during activation of the top and bottom electrodes.

According to another aspect of the present disclosure a system for measuring dielectric properties of biological tissue is disclosed. The system includes a top electrode assembly and a bottom electrode assembly. The top electrode assembly includes a top electrode and at least one shaft adjustably positionable to move the top electrode relative to the bottom electrode assembly. The bottom electrode assembly includes a testing plate configured to receive the tissue and a bottom electrode. The system also includes a testing cylinder coupled to the shaft. The testing cylinder includes an inner cavity defined therein that houses the top electrode and is designed to enclose the bottom electrode therein. The testing cylinder is configured to reduce at least one of electric current, magnetic current, stray radiative RF fields and external capacitive leakage currents during activation of the top and bottom electrodes. The system further includes a high frequency electrosurgical generator configured to supply high frequency electrical energy to the tissue through at least one of the top electrode and the bottom electrode and an analyzer configured to measure the properties of biological tissue in response to high frequency electrical energy.

According to yet another aspect of the present disclosure, a system for measuring the dielectric properties of material is disclosed. The system includes a top electrode assembly and a bottom electrode assembly. The top electrode assembly includes a top electrode and at least one shaft adjustably positionable to move the top electrode relative to the bottom electrode assembly. The bottom electrode assembly includes a testing plate configured to receive the material and a bottom electrode. The system also includes a testing cylinder coupled to the shaft and having an inner cavity defined therein that houses the top electrode and which is designed to enclose the bottom electrode therein. The testing cylinder is configured to reduce at least one of electric current, magnetic current, stray radiative RF fields and external capacitive leakage currents during activation of the top and bottom electrodes. The system also includes an analyzer configured to measure the properties of the material. The analyzer includes a generator configured to supply electrical energy to the material through at least one of the top electrode and the bottom electrode, wherein the analyzer is connected to the top electrode assembly, the bottom electrode assembly and the testing cylinder through a plurality of cables each having a wire, a shield and an insulator therebetween, the wires being connected to the top electrode and the bottom electrode and the shield being connected to the testing cylinder.

BRIEF DESCRIPTION OF THE DRAWINGS

Various embodiments of the subject instrument are described herein with reference to the drawings wherein.

DETAILED DESCRIPTION

Referring initially to FIGS. 1, 2, 3 and 5, one embodiment of a surgical testing instrument 100 is shown in an open position. Testing instrument 100 includes an L-shaped support base 106 having a back plate 106a and an elongated flange 106b extending from a bottom end thereof. A bracket support 106c is positioned between the back plate 106a and the elongated flange 106b to provide additional support to the support base 106. An elongated rib 107 extends from the back plate 106a parallel to flange 106b. Rib 107 includes a top portion 107a that is configured to support a top electrode assembly 140 and a bottom portion 107b that abuts against a bottom electrode assembly 150.

Support unit 106 and rib 107 may be constructed of a rigid material capable of providing structural support. Support base 106 and rib 107 may be constructed from a variety of different materials, including, but not limited to, metallic, ceramic, polymeric and wooden materials.

Top electrode assembly 140 includes a coupler 141 that securely engages the top portion 107a of rib 107 and is configured to include a lumen 141a defined therein (see FIG. 5) for slidingly receiving an elongated shaft 144. Elongated shaft 144 includes a slide rod 144a that securely mates with an electrode mandrel 144b, which in turn, secures an electrode 142 for testing dielectric properties of matter (e.g., living tissue). Mandrel 144b may include a top portion 144b' with a different or ergonomically-friendly geometry to facilitate handling thereof, e.g., for mounting the electrode 142 to the mandrel 144b.

Top electrode assembly 140 also includes first and second cylinders 145a and 145b that concentrically mate to receive and secure the electrode 142 and mandrel therein for testing purposes. More particularly, cylinder 145b includes a two-staged inner lumen 145b" defined therein (See FIG. 5) that is dimensioned to receive a mounting collar 147 in the lower portion thereof and elongated shaft 144 in the upper portion thereof. Mounting collar 147, in turn, includes a centrally disposed lumen 147' dimensioned to receive and secure the electrode 142 and the bottom portion of the mandrel 144b.

The first cylinder 145b is formed from a suitable conductive material such as copper, stainless steel, chromium, nickel, or an alloy which is any combination of these and similar metals and the like. The second cylinder 145b is formed from a suitable dielectric material having desirable insulative properties, such as Teflon and the like. The cylinder 145b is dimensioned such that it occupies substantially the entirety of the lumen of the first cylinder 145a to ensure that the space between the testing sample, the electrodes, and the first cylinder 145b is not occupied by air or other foreign substances. It has been determined that arranging the cylinders 145a and 145b in this fashion removes errors generated during testing which are caused by the electrical test signals passing through surrounding atmosphere (e.g., arcing conditions through air). In lieu of the second cylinder 145b various other dielectric solid and non-solid materials may be used (e.g., liquid). Those skilled in the art will appreciate the modifications which have to be made to the disclosed electrode and cylinder configurations to accommodate liquid insulators.

Cylinder 145b also includes an aperture 149b defined therein that is dimensioned to receive a pin 146 that is movable from a first position to secure the electrode 142 and mandrel 144b within cylinder 145b to a second position that releases the mandrel 144b and electrode 142 from within the cylinder 145b. Cylinder 145a is designed to concentrically mate with cylinder 145b and includes an aperture 149a defined therein that aligns with aperture 149b to facilitate access to pin 146. Mounting collar 147 also includes an aperture 147a defined therethrough that receives locking element 146a of pin 146 that optionally locks the electrode 142 in place for testing. The mounting collar 147 is formed from a conducting material, such as copper, stainless steel, chromium, nickel, or an alloy which is any combination of these and similar metals and the like. The mounting collar 147 is in physical and electrical contact with the electrode 142. During operation, electrical signals are passed to the electrode 142 through the pin 146 and the locking collar 147. The electrode 142 may be disposed slidingly within the mounting collar 147 allowing for selective adjustment of the vertical position and pressure of the electrode 142 on the testing sample. A plate 148 encloses the top of cylinder 145a. The plate 148 includes a through hole 148a defined therein that permits the elongated shaft 144 to slide therethrough during testing and/or mounting of the electrode 142.

Bottom electrode assembly 150 includes mounting plate 152 having a series of apertures 152a defined therein (See FIG. 3) that align with corresponding apertures 106d to secure the bottom electrode 150 to flange 106b. For example, apertures 152a are configured to receive locking mechanisms (not shown) such as pins, bolts, screws or the like to secure the bottom electrode assembly 150.

Circular coupling unit 154 is operatively connected to mounting plate 152 and defines an aperture 154a that is configured to receive a pin 156. Coupling unit 154 is configured to receive a circular washer 158 that is operatively connected to coupling unit 154 by way of a thread-fit, snap-fit or other mating arrangement. Circular washer 158 may define a groove 158a that is configured to hold ring 160. Tubular member 162 is configured to extend longitudinally within ring 160 and includes aperture 162a. Tubular member 162 is generally circular in nature and is configured to receive cylindrical member 164. Cylindrical member 164 includes a hole 164a that aligns with hole 154a to receive pin 156. Cylindrical member 164 also includes a passageway 164b defined in a top portion thereof that is dimensioned to receive electrode 166 therein. Electrode 166 is operatively connected with inner testing ring 168 and is configured to hold tissue therein.

Pin 156 extends through coupling unit 154, tubular member 162 and cylindrical member 164, and more particularly, through aperture 154a, aperture 162a and hole 164a. Pin 156 includes locking element 156a that is configured to secure cylindrical member 164 within bottom electrode assembly 150, more particularly, locking element 156a is movable from a first position to secure bottom electrode 166 within cylindrical member 164 to a second position that releases bottom electrode 166 from cylindrical member 164. During operation, electrical signal are passed to or from the electrode 166 through the pin 156 and the cylindrical member 164. Those skilled in the art will appreciate that the electrodes 142 and 166 may be used interchangeably as active or return electrodes.

As mentioned above, top electrode 142 is coupled to shaft 144 and is adjustably positionable to move in a general vertical direction. Bottom electrode 166 is housed within inner testing ring or plate 168 and is connected to cylindrical member 164. Inner testing plate 168 includes a lumen 169 which serves as an insert cavity to house the testing sample being measured. The testing plate 168 may be constructed out of a variety of different materials including, but not limited to, suitable insulated material, such as Teflon and the like. Testing plate 168 may also be configured to prevent tissue from expanding or deforming in any direction, therefore providing a more even tissue distribution. Testing plate 168 may be circular, square, oval or any other suitable shape and may be selectively formable for a particular tissue type. Moreover, testing plate 168 may rest upon bottom electrode 166 or include one or more mechanical interfaces that facilitate alignment with bottom electrode 166.

Electrodes 142, 166 are configured to move in substantial vertical registration relative to one another for testing purposes. Top and bottom electrodes 142, 166 may be detachably mounted to apparatus 100 to accommodate for sterilization and tissue preparation. Top and bottom electrodes 142, 166 may be constructed out of a number of different materials including, but not limited to, stainless steel, copper, brass, cobalt-based alloy, titanium, copper, chromium, nickel, or an alloy which is any combination of these and similar metals and the like. These materials can be readily sterilized and are used in medical devices due to their anti-corrosive properties.

As mentioned above, cylinders 145a and 145b surround electrode 142. The second cylinder 145b is constructed of an insulative material that is designed to eliminate or reduce stray capacitance, which is a major cause of measurement error in surgical testing equipment, particularly those that deal with dielectric materials. As explained in more detail below, when the testing unit is moved from an open tissue mounting position to the testing position, cylinders 145a and 145b surround both electrodes 142 and 166. The insulative material may be selected from a variety of different materials, including, but not limited to, polymerics, ceramics and glass.

Figure 1:
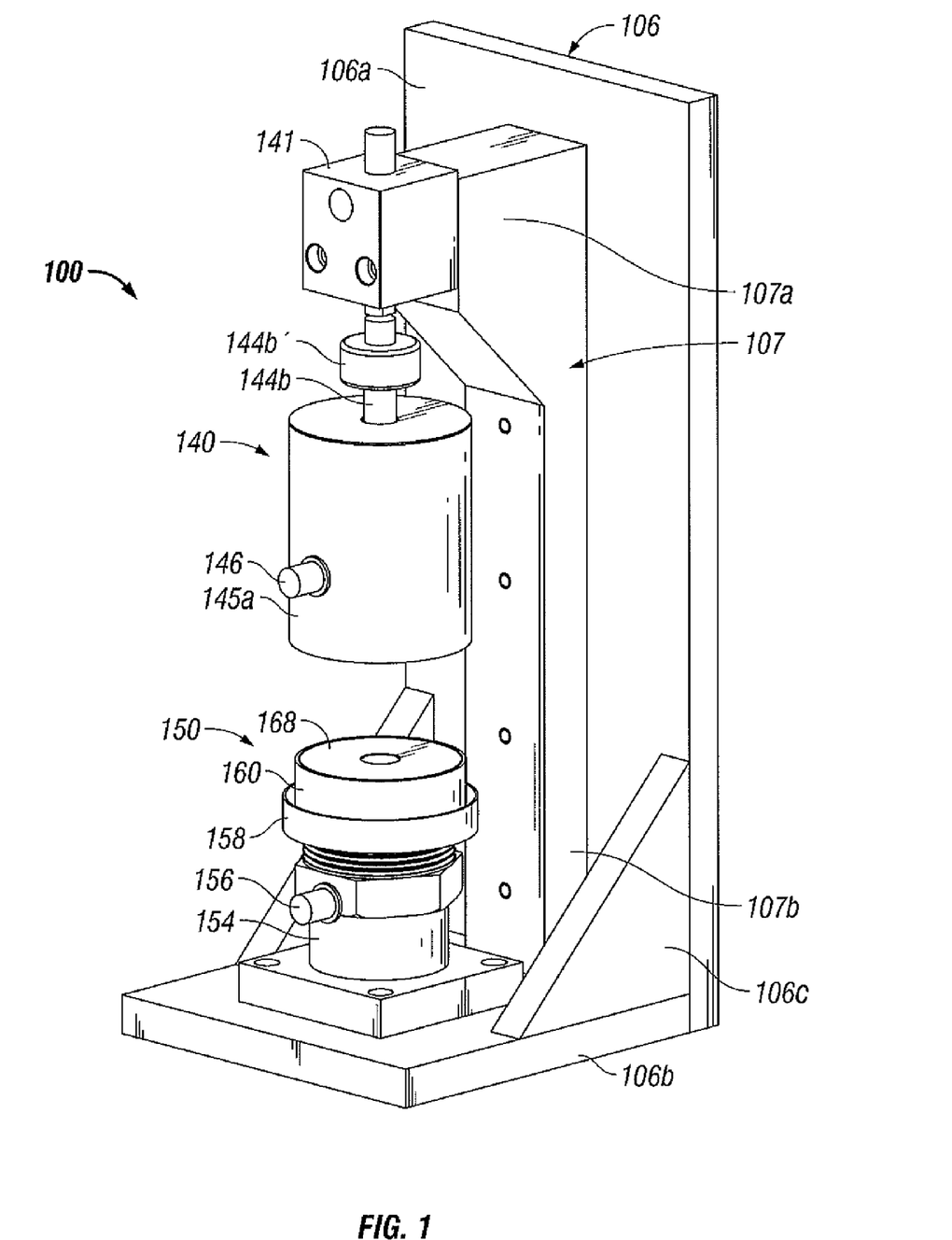
FIG. 1 is a perspective view of one embodiment according to the present disclosure shown in an open position.
Figure 2:
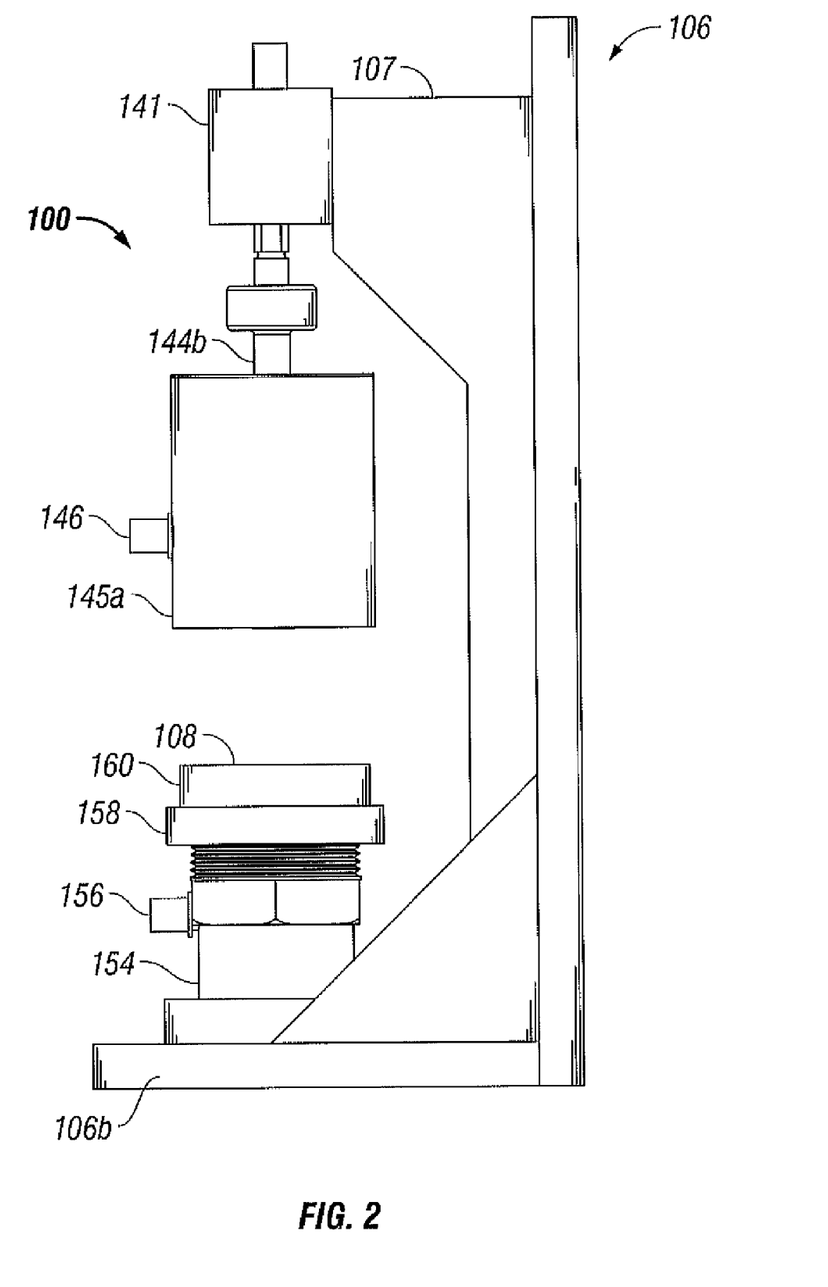
FIG. 2 is a side perspective view of the instrument shown in FIG. 1.
Figure 3:
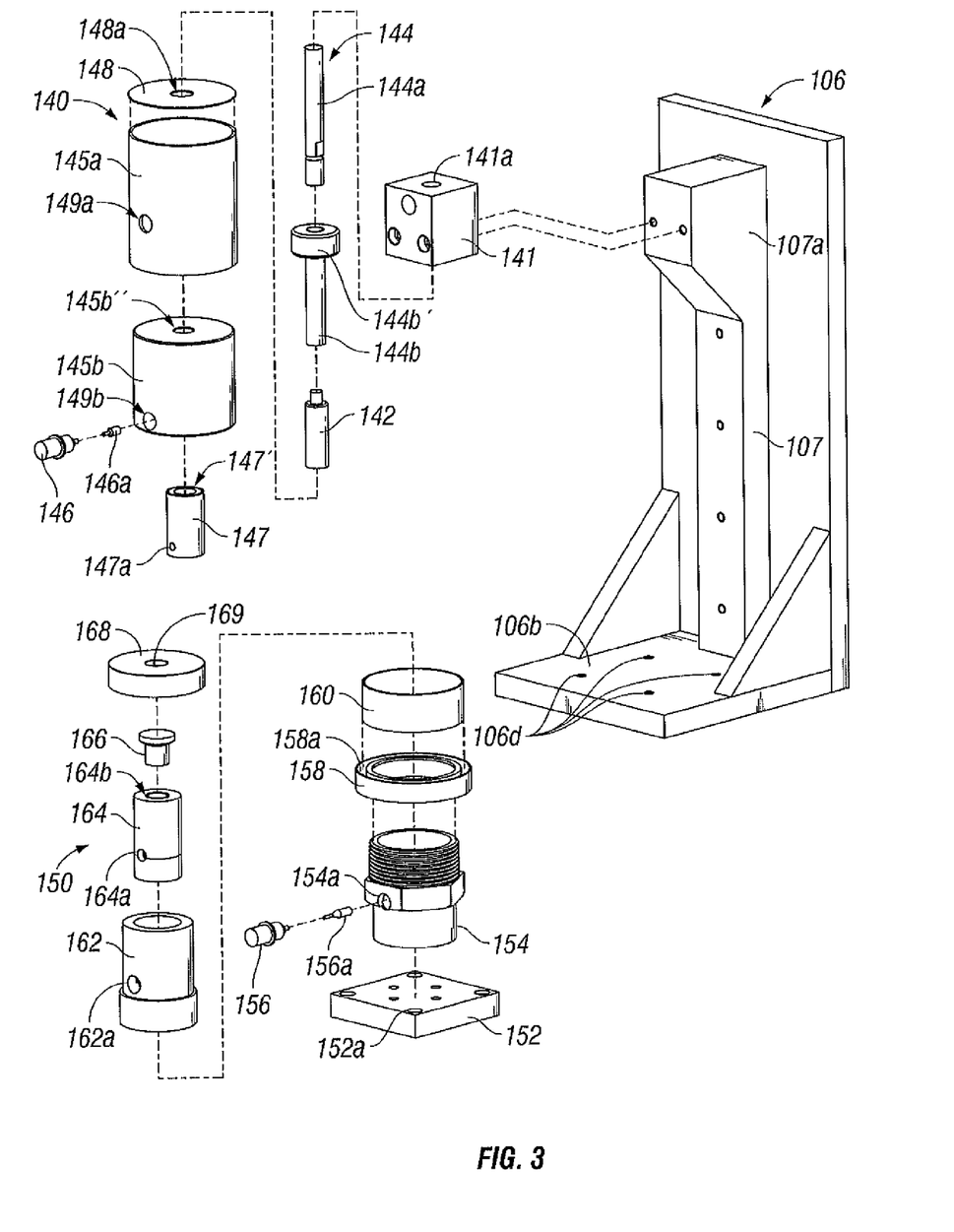
FIG. 3 is an exploded view of the instrument shown in FIGS. 1-2.
Figure 4:
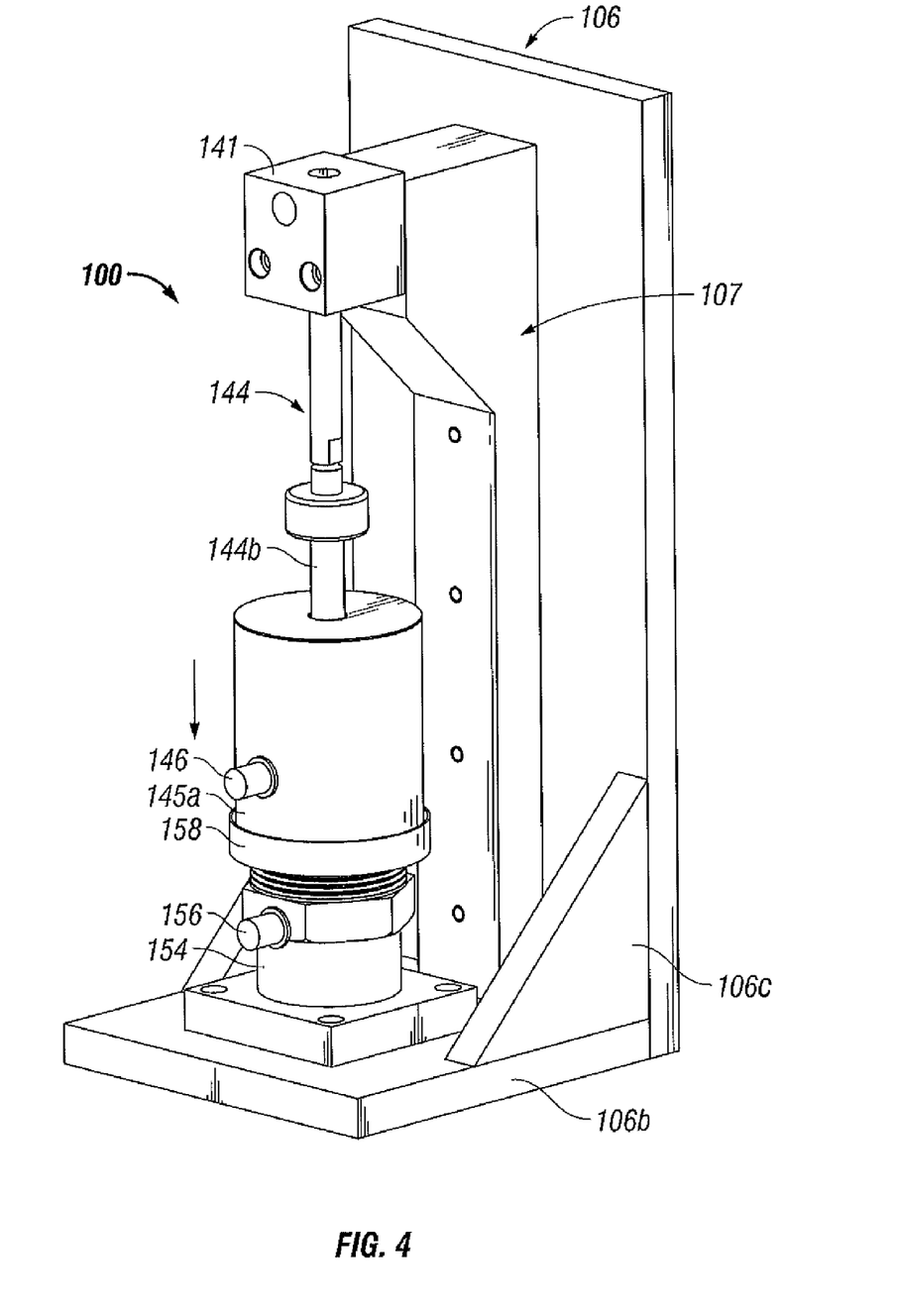
FIG. 4 is a perspective view of the instrument shown in FIGS. 1-3 shown in the closed position.
Figure 5:
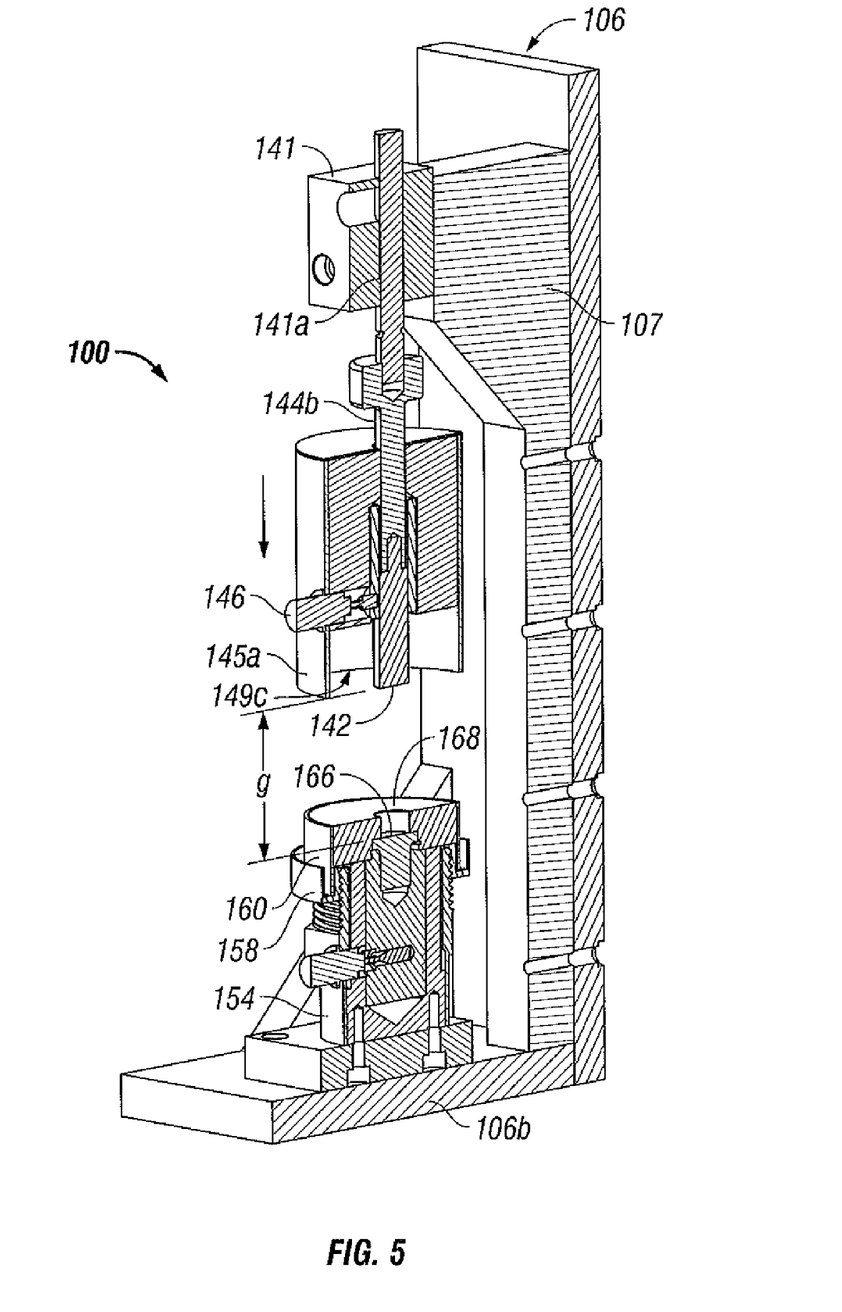
FIG. 5 is a cross-sectional view of the instrument shown in FIGS. 1-4 shown in the open position.
Figure 6:
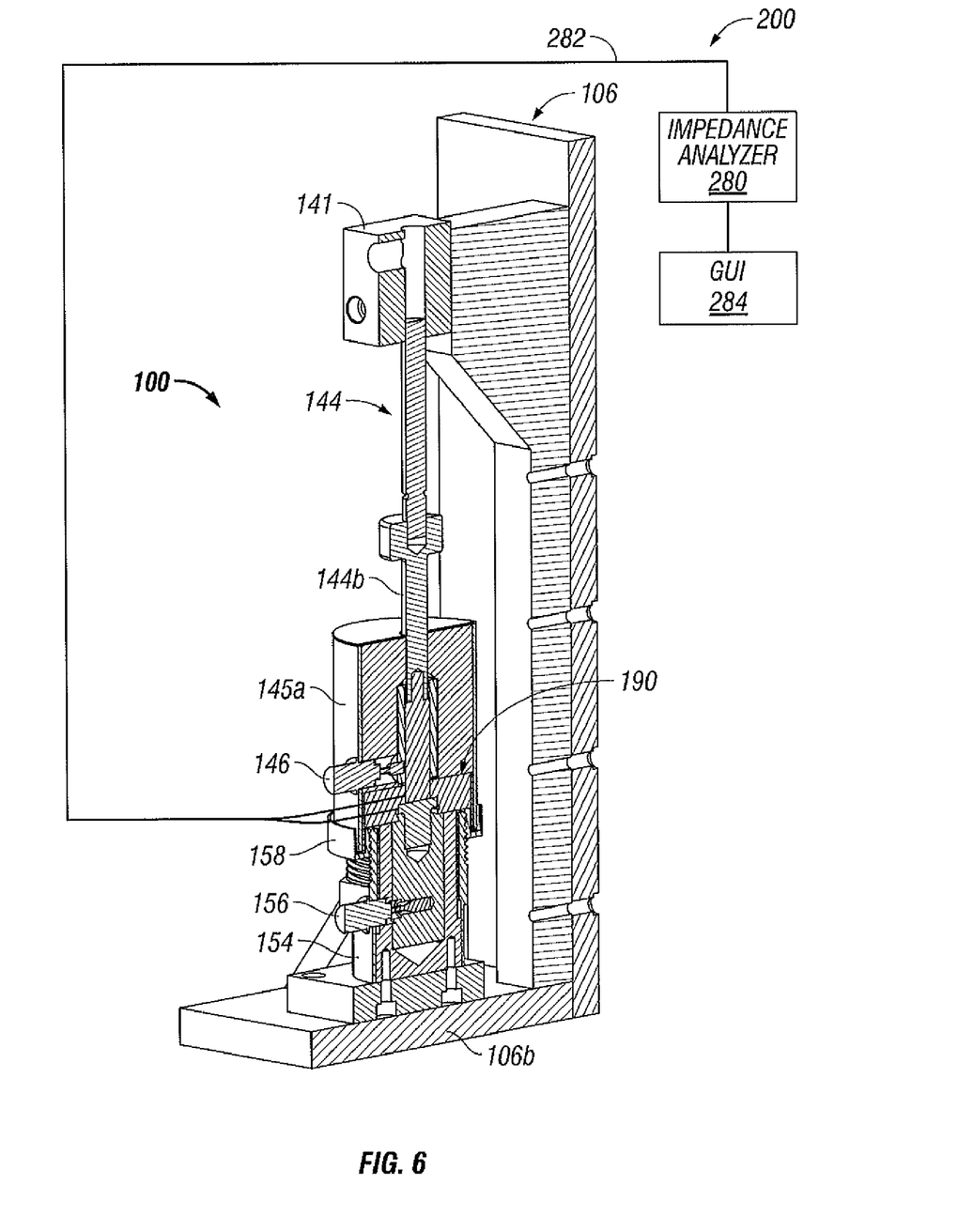
FIG. 6 is a cross-sectional view of another embodiment of the system according to the present disclosure.

FIGS. 2 and 5 show the testing unit 100 in an open position for loading tissue and FIGS. 4 and 6 show the testing unit 100 in a closed position for testing tissue. More particularly, once the two electrodes 142 and 166 are assembled in their respective top and bottom electrode assemblies 140 and 150 as shown in FIG. 3, the testing unit 100 is readied to receive and test tissue. In the open position, cylinders 145a and 158 reside in generally vertical registration relative to one another for loading biological tissue atop testing plate 168.

Tissue is placed within the lumen 169 and is shaped to ensure that the tissue occupies the entire volume of the thereof so that the tissue sample is in substantially complete contact with the electrodes 142 and 166. This may be accomplished by initially placing an excessive amount of the tissue sample into the lumen 169 and then cutting the excess tissue to fit the lumen. Cutting may be accomplished by sliding a cutting instrument (e.g., scalpel) along the periphery of the top surface of the testing plate 168 thereby using the surface as a guide to ensure that the tissue sample occupies the lumen 169. To further ensure that tissue contact between the electrodes 142 and 166 is thorough (e.g., no empty space exists between the sample and the electrodes) hydrogel inserts may be placed therebetween.

Electrodes 142 and 166 could be constructed into a variety of different shapes including, but not limited to, circular, square, polygonal and oval. Moreover, electrodes 142 and 166 could have varying degrees of thickness. Electrodes 142 and 166 also include a connection through the pins 146 and 156 that allows the electrodes to connect with cables, which are discussed below. The electrodes 142 and 166 and the testing plate 168 are detachable and can have various shapes such that the shape of the lumen 169 (e.g., the insert cavity) is selectively conformable to various types of tissue and/or materials being tested. The modular construction of the instrument 100, in particular the electrodes 142 and 166 and the testing plate 168 also allows for easy cleaning and sterilization of these components. Thus an insert cavity having a cylindrical shape may be used for testing liver tissue, whereas a rectangular shaped cavity may be used for testing dielectric materials.

Once the tissue is placed into the testing plate 168, the testing unit 100 may be moved to the so-called testing position. More particularly, when the user is ready to test the tissue, the user manipulates the shaft 144 (e.g., by moving mandrel 144b towards the bottom electrode assembly 150), which in turn, moves the cylinder 145a relative to cylinder 158 to enclose the tissue within the inner cavity 149c defined in cylinder 145a around electrode 142 (see FIGS. 4 and 6). In the closed position, electrode 142 and 166 are positioned to engage the tissue for testing purposes. Moreover, when cylinders 145a and 158 meet, the cylinders 145a and circular washer 158 form an enclosure or shield 190 around the electrodes 142 and 166 and the tissue. In one particular embodiment, the cylinder 145a with a bottom portion (e.g., the circular washer 158 and the ring 160) act as a Faraday cage to reduce or eliminate stray magnetic fields during activation which as mentioned above, allows the test fixture to obtain more reliable and accurate results.

In the closed testing position, the vertical position of the electrode 142 may be adjusted to apply variable mechanical pressure on the tissue sample within the testing plate 168 to ensure that the tissue contact is maintained between tissue and the electrodes 142 and 166. This also removes any empty space (e.g., air) within the lumen 169. The tissue engaging surface of the electrodes may also be polished to assure continuity with the tissue for testing purposes.

The coupler 141 guides the elongated shaft 144 and allows for vertical positioning of the electrode 142. In particular, vertical position of the electrode 142 is directly related to the compression and/or pressure exerted on the testing sample. The coupler 141 may include a pressure transducer (not explicitly shown) or another apparatus (e.g., graphical scale) for measuring the pressure exerted by the electrode 142 on the testing sample. This allows for testing effects of pressure on the dielectric properties of the testing sample. In particular, by varying pressure during testing, the relationship between viscoelastic properties and tissue conductivity and permeability may be tested.

FIG. 5 shows instrument 100 held in the open position having an extended gap distance "g". The gap distance "g" between electrodes 142 and 166 may be controlled using adjustable mechanism or pin 146. Testing instrument 100 may be adjusted, using this mechanism, between open, closed and various measurement positions respectively. Alternatively, FIG. 6 shows instrument 100 in the closed position having a reduced gap distance "g". Adjustable mechanism 146 may include knobs, latches, switches, levers or any other suitable device configured to alter the gap distance "g" between electrodes 142 and 166.

Referring again to FIGS. 6-7, instrument 100 may be used as part of a system 200 that includes an impedance analyzer 280, a plurality of connection cables 282 and a graphical user interface 284. Dielectric testing is used to determine the frequency response of the permittivity and conductivity of a material. This means that the material will be exposed to a specific frequency from a voltage source while the current flowing through the material is measured. From this information, the magnitude of the impedance and the phase shift between the voltage and current time signals is determined. This entire process is repeated at different frequencies so that a graph of magnitude of impedance vs. frequency and a graph of phase vs. frequency for a given material can be created. Impedance analyzer 280 is configured to perform these tests. In addition to displaying the impedance and phase of a material at a specific excitation frequency, analyzer 280 also has the capability of outputting various equivalent forms of the impedance and phase of a test material.

Figure 7:
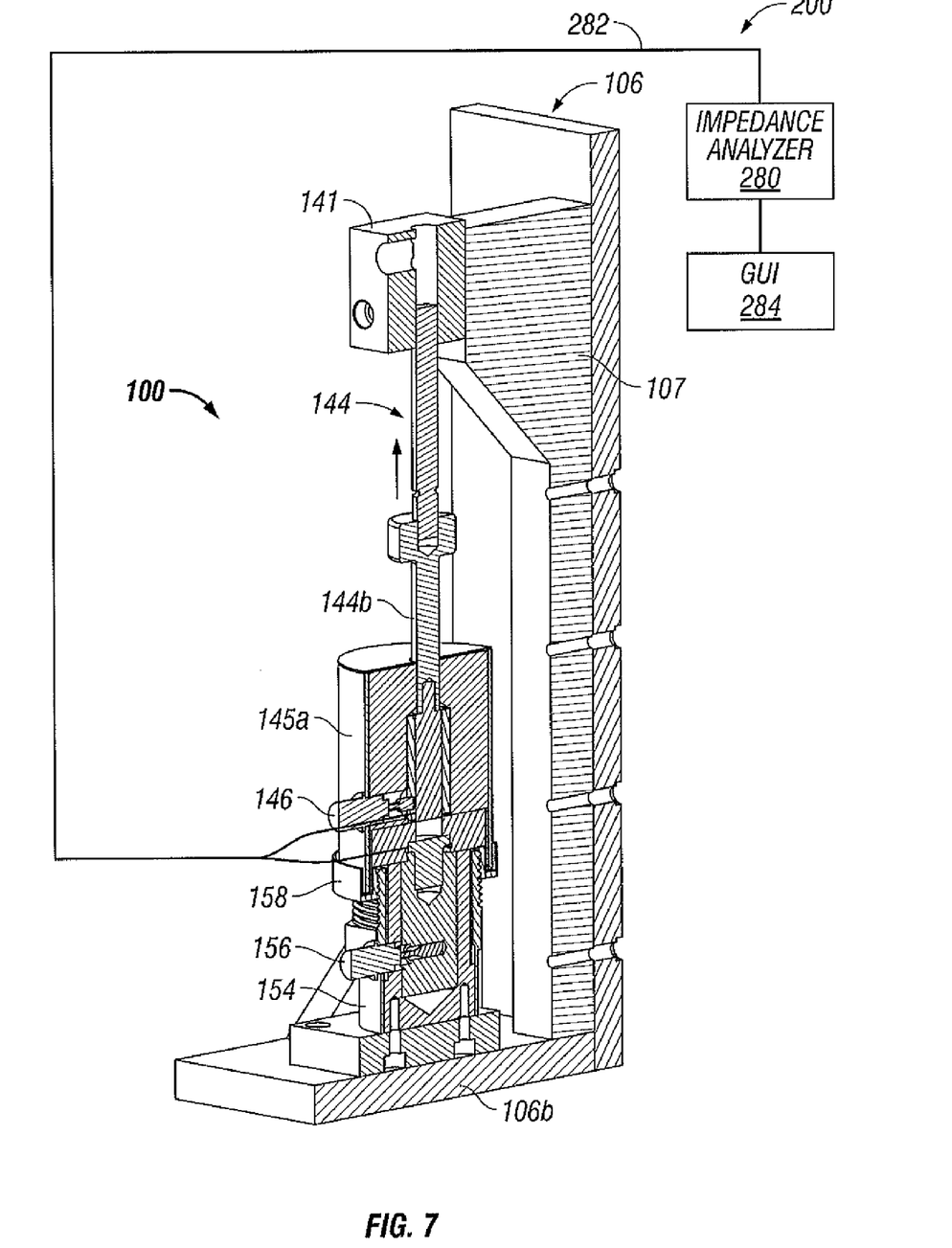
FIG. 7 is a cross-sectional view of the system of FIG. 6 shown being actuated.

Analyzer 280 is configured to measure a variety of different parameters of biological tissue. Some of these may include, but are not limited to, gain, phase, capacitance, impedance, conductance, dissipation factor and loss tangent. Analyzer 280 is controlled using a graphical user interface (GUI) 284 that is configured to control analyzer 280 through a communications port, such as a general purpose interface bus (GPIB). Connection cables 282 are configured to connect impedance analyzer 280 with top and bottom electrodes 142 and 166.

Figure 8:
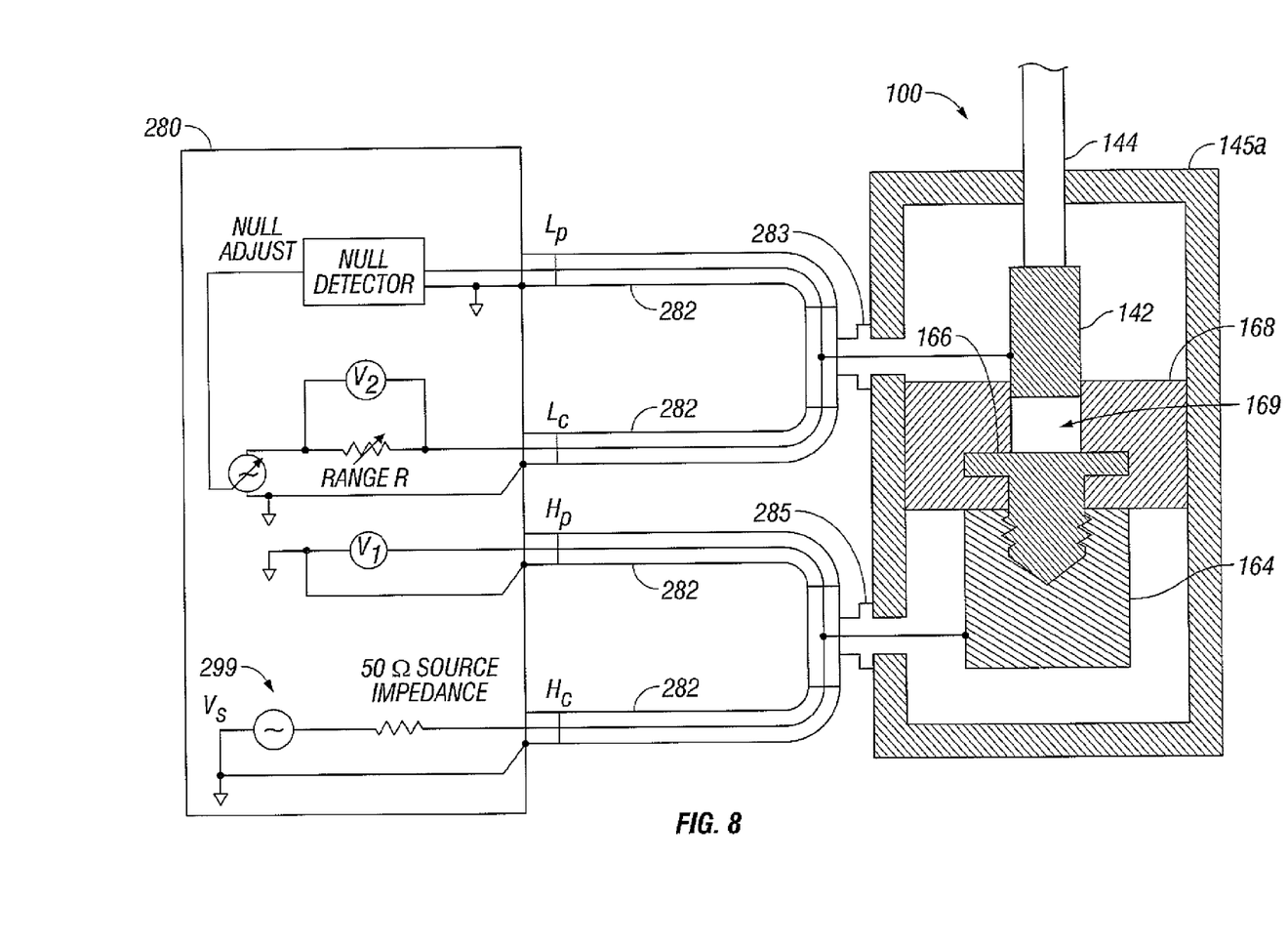
FIG. 8 is a schematic illustration of the present disclosure.

Referring now to FIG. 8 an electrical schematic of the impedance analyzer 280 connected to the instrument 100. Connection or BNC cables 282 are commonly used to transmit electrical signals. BNC cables 282 carry the signal along a wire on the axis of the cable. This wire is surrounded with an insulator, which is wrapped with a braided shield. Normally, this shield is connected to ground via the BNC connector at the ends of the cable, although the connectors may allow the shield to "float" to varying voltages. The shield is very helpful in isolating the inner conductor from stray RF and capacitive leakage fields as well as any magnetic fields, which would produce noise.

BNC cables 282 are used to eliminate the effect of test signal losses in cables 282 as well as to match the impedance of cables 282 to the impedance of instrument 200. The signal loss of BNC cables 282 is minimized by monitoring the signal at the tissue under test and providing corrective compensation at the signal source at the cable, which contributes frequency dependent errors to the measurement of tissue conductivity and permittivity.

As shown in FIG. 8, the outer shields of the low potential and current (Lp and Lc) terminals are connected to a BNC-T connector 283 which is then connected to the pin 146. The high potential and high current (Hp and Hc) terminals are connected to a BNC-T connector 285 which is then connected to the pin 156. As discussed above, the pin 146 is electrically connected to the electrode 142 and the pin 156 is electrically connected to the electrode 166. The BNC-T connectors 283 and 285 include wire interconnects and shield interconnects which are insulated from one another. The BNC-T connectors 283 and 285 and the pins 146 and 156 connect the wires of the BNC cables 282 to the respective electrodes 142 and 166 while the ground shielding of the BNC cables 282 are connected to the first cylinder 145a and the coupling unit 154. As a result, the first cylinder 145a in conjunction with the circular washer 158 and the ring 160 act as a cylindrical RF shield containment vessel which provides continuity for the coaxial outer shields and a low-impedance low-loss signal return path independent of tester operating frequency. In particular, the RF shield containment vessel reduces stray radiative RF fields and external capacitive leakage components which are known to corrupt measurement integrity and introduce significant error.

Analyzer 280 has four output terminals across which instrument 100 is connected. There are five different available configurations for connecting instrument 100 to analyzer 280, all of which have varying levels of accuracy and setup difficulty. The most accurate of the five methods is called the four terminal pair (4TP) configuration.

Figure 9A:
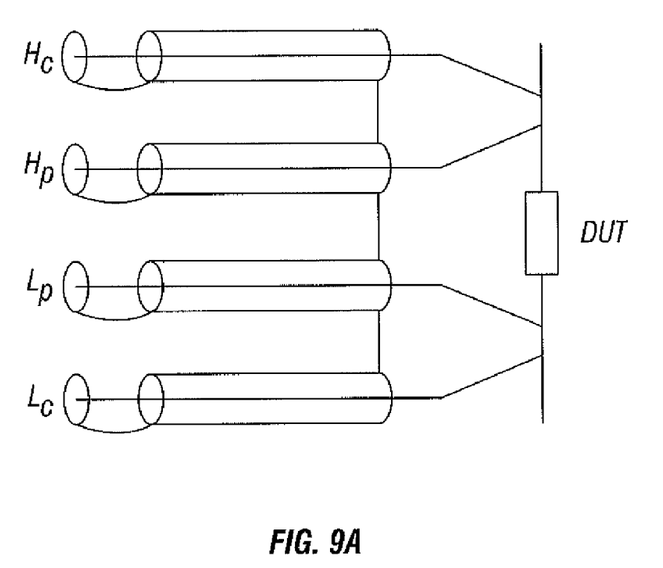
FIGS. 9a-c are electrical schematic illustrations of the present disclosure showing four terminal pair connections.
Figure 9B:
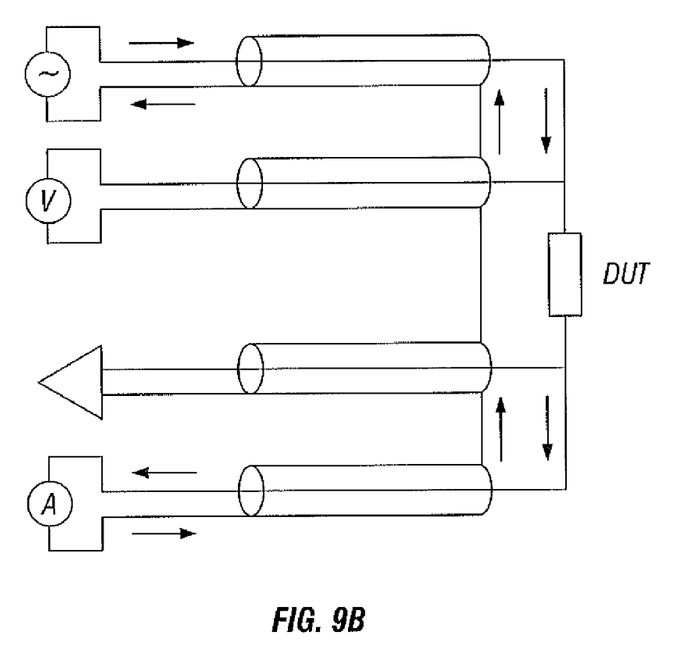

FIGS. 9A-B show a connection diagram and a schematic of the 4TP connection setup. Four-terminal pair wiring provides localized tissue metering to minimize fixture error. The current flows out of the digital signal generator or analyzer 280 at the high current (Hc) terminal and into instrument 100, the device under test (DUT). The Hc terminal is connected to an AC generator 299. From there, the current flows into the low current (Lc) terminal where an ammeter measures only the current that flows through the electrode connected to the Lc terminal or top electrode 142. The low voltage side of the ammeter is connected to the measuring circuit ground. The measuring circuit ground level is referred to as the "guard ground." This guard ground is connected back to the digital signal generator or analyzer 280 and is also connected to the ground sheaths of the four output BNC terminals of analyzer 280. The connections shown in FIG. 9 are made with BNC connectors, and the outer conducting sheath of each BNC cable is connected together. This means that the return current flowing through cables 282 is the same as the current flowing through the inner cable of the BNC connector, thus canceling any field effect caused by the inner cable.

Figure 9C:
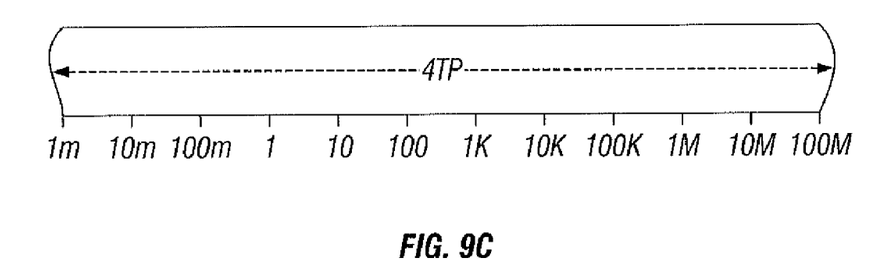

FIG. 9C shows the typical impedance measurement range, shown in ohms (Ω). Analyzer 280 utilizes an auto balancing bridge to detect the impedance across instrument 100. Analyzer 280 measures the magnitude of the impedance as well as the phase difference between the applied AC voltage and the measured AC current. Analyzer 280 measures the current present at top electrode 142. A measurement signal is always produced at bottom electrode 166 while top electrode 142 is continually maintained at a OV potential by analyzer 280.

The AC generator 299 (which provides electrical signals through the Hc terminal) may be an electrosurgical generator or any generator capable of producing high frequency energy since the RF shield allows for high frequency RF energy to be applied to the testing samples. Conventional testing apparatuses lacked shielding and as a result could only use low energy electrical signals. The instrument 100 allows for use of high frequency RF energy (e.g., 100 kHz-1000 kHz) to be applied to the tissue samples due to RF shielding provided by the first cylinder 145a in conjunction with the circular washer 158 and the ring 160. This is particularly useful for testing tissue reaction to electrosurgical energy (e.g., high frequency RF energy) during operating conditions.

Instrument 100 in some instances may utilize portions of ASTM standard D 150-98 entitled "Standard test methods for AC loss characteristics and permittivity (Dielectric Constant) of solid electrical insulation" when possible to determine testing methodologies. Since biological tissue is not a solid electrical insulator, several of the techniques described in the standards may not be directly applicable to measuring the dielectric properties of tissue but may be useful in achieving more accurate results.

Modeling packages, such as those that utilize finite element analysis, may be used to assist in modeling heat transfer and electric fields during RF energy applications. One applicable finite element software system is known as Etherm. Etherm is used to model heating in biological media for electrosurgery and other medical applications. The electrical field component calculates penetration of RF radiation into conductive dielectrics. The information obtained from instrument 100 may be integrated into Etherm or a similar program to create a more accurate model.

A number of different graphical user interfaces (GUI's) could be utilized in this disclosure, one of which includes National Instruments' LabVIEW™. LabVIEW is a software tool for designing test, measurement and control systems. Use of a GUI, such as LabVIEW provides additional control over the operation of analyzer 280 and allows for more sophisticated simulation.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

The invention claimed is:

1. An instrument for measuring the dielectric properties of material, the instrument comprising:
   a top electrode assembly and a bottom electrode assembly, the top electrode assembly including a top electrode and at least one shaft adjustably positionable to move the top electrode relative to the bottom electrode assembly, the bottom electrode assembly including a bottom electrode;
   a testing cylinder coupled to the shaft and having an inner cavity defined therein that houses the top electrode and which is designed to enclose the bottom electrode therein, the testing cylinder being configured to reduce at least one of electric and magnetic currents during activation of the top and bottom electrodes; and
   a testing plate for receiving the testing material thereon includes a selectively conformable insert cavity therein, the testing plate being disposed between the top electrode assembly and the bottom electrode assembly.

2. An instrument as in claim 1, wherein the testing cylinder is further configured to reduce at least one of stray radiative RF fields and external capacitive leakage currents.

3. The instrument according to claim 1, wherein the top and bottom electrodes are constructed of at least one of the stainless steel, titanium, chromium or nickel.

4. An instrument as in claim 1, wherein the testing plate, the top electrode assembly and the bottom electrode assembly are selectively removable and detachably mounted.

5. The instrument according to claim 1, wherein the testing cylinder includes concentric outer and inner cylinders, the outer cylinder defining the internal cavity and the inner cylinder being formed from an insulative material that reduces at least one of electric and magnetic currents during activation.

6. The instrument according to claim 5, wherein the testing cylinder includes a bottom portion and the outer cylinder and the bottom portion of the testing cylinder are configured as a Faraday cage.

7. The instrument according to claim 1, further comprising a plurality of connection cables, the cables configured to connect an impedance analyzer with the top and bottom electrodes.

8. The instrument according to claim 7, wherein the impedance analyzer is configured to measure a parameter selected from the group consisting of gain, phase, capacitance, impedance, conductance and loss tangent.

9. The instrument according to claim 7, further comprising a graphical user interface (GUI), the GUI configured to control the analyzer through a communications port.

10. The instrument according to claim 7, further comprising:
    a pressure sensor configured to measure pressure exerted by the top electrode on the material, wherein the impedance analyzer is configured to measure a parameter of the material selected from the group consisting of gain, phase, capacitance, impedance, conductance and loss tangent as pressure is selectively adjusted.

11. An instrument for measuring the dielectric properties of material, the instrument comprising:
    a top electrode assembly and a bottom electrode assembly, the top electrode assembly including a top electrode and at least one shaft adjustably positionable to move the top electrode relative to the bottom electrode assembly, the bottom electrode assembly including a bottom electrode;
    a testing cylinder coupled to the shaft and having an inner cavity defined therein that houses the top electrode and which is designed to enclose the bottom electrode therein, the testing cylinder being configured to reduce at least one of electric and magnetic currents during activation of the top and bottom electrodes; and
    wherein the testing cylinder includes concentric outer and inner cylinders, the outer cylinder defining the internal cavity and the inner cylinder being formed from an insulative material that reduces at least one of electric and magnetic currents during activation for measuring the dielectric properties of material.

12. A system for measuring the dielectric properties of biological tissue, the system comprising:
   an analyzer configured to measure the properties of the biological tissue;
   a top electrode assembly and a bottom electrode assembly, the top electrode assembly including a top electrode and at least one shaft adjustably positionable to move the top electrode relative to the bottom electrode assembly, the bottom electrode assembly including a testing plate for receiving the biological tissue thereon and a bottom electrode; wherein the testing plate includes a selectively conformable insert cavity therein, the testing plate being disposed between the top electrode assembly and the bottom electrode assembly;
   a testing cylinder coupled to the shaft and having an inner cavity defined therein that houses the top electrode and which is designed to enclose the bottom electrode therein, the testing cylinder being configured to reduce at least one of electric and magnetic currents during activation of the top and bottom electrodes; and
   a graphical user interface configured to control the analyzer.

13. The system according to claim 12, wherein the testing cylinder is further configured to reduce at least one of stray radiative RF fields and external capacitive leakage currents.

14. The system according to claim 12, wherein the testing cylinder is a Faraday cage.

15. The system according to claim 12, wherein the testing plate, the top electrode assembly and the bottom electrode assembly are selectively removable and detachably mounted.

16. The system according to claim 12, further comprising at least one connection cable, the at least one cable configured to connect the impedance analyzer with the top and bottom electrodes.

17. The system according to claim 16, wherein the at least one cable utilizes a four terminal pair configuration to connect the analyzer and the top and bottom electrodes.

18. The system according to claim 16, wherein the analyzer is configured to measure a parameter selected from the group consisting of gain, phase, capacitance, impedance, conductance and loss tangent.

19. The system according to claim 16, a pressure sensor configured to measure pressure exerted by the top electrode on the material, wherein the impedance analyzer is configured to measure a parameter of the material selected from the group consisting of gain, phase, capacitance, impedance, conductance and loss tangent as pressure is selectively adjusted.

20. A system for measuring the dielectric properties of biological tissue, the system comprising:
   a top electrode assembly and a bottom electrode assembly, the top electrode assembly including a top electrode and at least one shaft adjustably positionable to move the top electrode relative to the bottom electrode assembly, the bottom electrode assembly including a testing plate configured to receive the tissue and a bottom electrode; wherein the testing plate includes a selectively conformable insert cavity therein, the testing plate being disposed between the top electrode assembly and the bottom electrode assembly;
   a testing cylinder coupled to the shaft and having an inner cavity defined therein that houses the top electrode and which is designed to enclose the bottom electrode therein, the testing cylinder being configured to reduce at least one of electric and magnetic currents during activation of the top and bottom electrodes;
   a high frequency electrosurgical generator configured to supply high frequency electrical energy to the tissue through at least one of the top electrode and the bottom electrode; and
   an analyzer configured to measure the properties of biological tissue in response to high frequency electrical energy.

21. A method for measuring the dielectric properties of biological tissue comprising the steps of:
   providing a top electrode assembly and a bottom electrode assembly, the top electrode assembly including a top electrode and at least one shaft adjustably positionable to move the top electrode relative to the bottom electrode assembly, the bottom electrode assembly including a testing plate for receiving the biological tissue thereon and a bottom electrode; wherein the testing plate includes a selectively conformable insert cavity therein, the testing plate being disposed between the top electrode assembly and the bottom electrode assembly;
   coupling a testing cylinder to the shaft, the testing cylinder having an inner cavity defined therein that houses the top electrode and which is designed to enclose the bottom electrode therein, the testing cylinder being configured to reduce at least one of electric and magnetic currents during activation of the top and bottom electrodes; and
   connecting an analyzer to the top electrode assembly and the bottom electrode assembly, the analyzer being configured to measure and analyze the dielectric properties of biological tissue.

22. A method for measuring the dielectric properties of biological tissue comprising the steps of:
   providing a top electrode assembly, a bottom electrode assembly and a testing plate, the top electrode assembly including a top electrode and at least one shaft adjustably positionable to move the top electrode relative to the bottom electrode assembly, the bottom electrode assembly including a bottom electrode, and the testing plate being disposed between the top electrode assembly and a bottom electrode assembly and including a selectively conformable insert cavity therein;
   inserting a tissue sample into the selectively conformable insert cavity and forming the tissue sample by cutting any excess tissue to fit the tissue sample into the insert cavity; and
   coupling a testing cylinder to the shaft, the testing cylinder having an inner cavity defined therein that houses the top electrode and which is designed to enclose the bottom electrode therein, the testing cylinder being configured to reduce at least one of electric and magnetic currents during activation of the top and bottom electrodes.

23. A method according to claim 22, further comprising the step of:
   applying selective pressure onto the tissue sample by lowering the shaft and placing the top electrode in contact with the tissue sample.

24. A system for measuring the dielectric properties of material, the system comprising:
   a top electrode assembly and a bottom electrode assembly, the top electrode assembly including a top electrode and at least one shaft adjustably positionable to move the top electrode relative to the bottom electrode assembly, the bottom electrode assembly including a testing plate configured to receive the material and a bottom electrode; wherein the testing plate includes a selectively conformable insert cavity therein, the testing plate being disposed between the top electrode assembly and the bottom electrode assembly;

a testing cylinder coupled to the shaft and having an inner cavity defined therein that houses the top electrode and which is designed to enclose the bottom electrode therein, the testing cylinder being configured to reduce at least one of electric and magnetic currents during activation of the top and bottom electrodes; and an analyzer configured to measure the properties of the material, the analyzer including a generator configured to supply electrical energy to the material through at least one of the top electrode and the bottom electrode, wherein the analyzer is connected to the top electrode assembly, the bottom electrode assembly and the testing cylinder through a plurality of cables each having a wire, a shield and an insulator therebetween, the wires being connected to the top electrode and the bottom electrode and the shield being connected to the testing cylinder.

25. A system according to claim 24, further comprising:

a plurality of T connectors each of which includes a wire interconnect, a shield interconnect and an insulator, the T connectors electrically and mechanically couple the plurality of cables to the at least one of top electrode assembly, the bottom electrode assembly and the testing cylinder.

* * * * *